(12) United States Patent
Sybert et al.

(10) Patent No.: US 8,252,056 B2
(45) Date of Patent: *Aug. 28, 2012

(54) BIOCOMPATIBLE OSTEOGENIC BAND FOR REPAIR OF SPINAL DISORDERS

(75) Inventors: Daryl R. Sybert, New Ablany, OH (US); Lawrence A. Shimp, Morganville, NJ (US); Todd M. Boyce, Matawan, NJ (US); John W. Boyle, Upper Montclair, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 90 days.

This patent is subject to a terminal disclaimer.

(21) Appl. No.: 12/885,818

(22) Filed: Sep. 20, 2010

(65) Prior Publication Data
US 2011/0046677 A1 Feb. 24, 2011

Related U.S. Application Data

(63) Continuation of application No. 12/193,534, filed on Aug. 18, 2008, now Pat. No. 7,799,076, which is a continuation of application No. 10/850,149, filed on May 20, 2004, now Pat. No. 7,413,576, which is a continuation of application No. 09/733,327, filed on Dec. 8, 2000, now Pat. No. 6,752,831.

(51) Int. Cl.
*A61F 2/44* (2006.01)
*A61F 2/08* (2006.01)

(52) U.S. Cl. .................................. 623/17.11; 623/13.17

(58) Field of Classification Search .................. None
See application file for complete search history.

(56) References Cited

U.S. PATENT DOCUMENTS

| | | | |
|---|---|---|---|
| 4,202,055 A | 5/1980 | Reiner et al. |
| 4,294,753 A | 10/1981 | Urist |
| 4,713,076 A | 12/1987 | Draenert |
| 4,834,757 A | 5/1989 | Brantigan |
| 4,877,864 A | 10/1989 | Wang et al. |
| 4,878,915 A | 11/1989 | Brantigan |
| 4,902,508 A | 2/1990 | Badylak et al. |
| 5,013,649 A | 5/1991 | Wang et al. |
| 5,073,373 A | 12/1991 | O'Leary et al. |
| 5,092,887 A | 3/1992 | Gendler |
| 5,106,748 A | 4/1992 | Wozney et al. |
| 5,108,922 A | 4/1992 | Wang et al. |
| 5,116,738 A | 5/1992 | Wang et al. |
| 5,171,273 A | 12/1992 | Silver et al. |
| 5,187,076 A | 2/1993 | Wozney et al. |
| 5,243,038 A | 9/1993 | Ferrari et al. |

(Continued)

FOREIGN PATENT DOCUMENTS

WO    WO 93/00432    1/1993

(Continued)

OTHER PUBLICATIONS

Jürgensen, et al., "A New Biological Glue for Cartilage-Cartilage Interfaces: Tissue Transglutaminase", *Journal of Bone and Joint Surgery*, vol. 79-A, No. 2, pp. 185-193 (Feb. 1997).

(Continued)

*Primary Examiner* — Suzette J Gherbi (57) ABSTRACT

Methods of repairing a joint formed by at least two bone sections are provided wherein a biocompatible osteogenic band fabricated from an osteogenic biological material such as bone, tendon, ligament and collagen is affixed to two or more bone sections.

27 Claims, 5 Drawing Sheets

U.S. PATENT DOCUMENTS

| | | | |
|---|---|---|---|
| 5,263,984 A | 11/1993 | Li et al. | |
| 5,314,476 A | 5/1994 | Prewett et al. | |
| 5,366,875 A | 11/1994 | Wozney et al. | |
| 5,378,469 A | 1/1995 | Kemp et al. | |
| 5,393,594 A | 2/1995 | Koyfman et al. | |
| 5,405,390 A | 4/1995 | O'Leary et al. | |
| 5,496,318 A | 3/1996 | Howland et al. | |
| 5,507,810 A | 4/1996 | Prewett et al. | |
| 5,507,813 A | 4/1996 | Dowd et al. | |
| 5,522,841 A | 6/1996 | Roby et al. | |
| 5,549,676 A | 8/1996 | Johnson | |
| 5,705,181 A | 1/1998 | Cooper et al. | |
| 5,895,428 A | 4/1999 | Berry | |
| 5,899,939 A | 5/1999 | Boyce et al. | |
| 5,962,427 A | 10/1999 | Goldstein et al. | |
| 5,972,368 A | 10/1999 | McKay | |
| 5,989,894 A | 11/1999 | Lewis et al. | |
| 6,045,580 A | 4/2000 | Scarborough et al. | |
| 6,048,964 A | 4/2000 | Lee et al. | |
| 6,090,988 A | 7/2000 | Kambe et al. | |
| 6,123,731 A | 9/2000 | Boyce et al. | |
| 6,311,690 B1 | 11/2001 | Jefferies | |
| 6,652,592 B1 * | 11/2003 | Grooms et al. | 623/23.51 |
| 6,752,831 B2 * | 6/2004 | Sybert et al. | 623/13.17 |
| 6,843,807 B1 * | 1/2005 | Boyce et al. | 623/23.51 |
| 6,863,694 B1 * | 3/2005 | Boyce et al. | 623/23.63 |
| 7,413,576 B2 * | 8/2008 | Sybert et al. | 623/13.17 |
| 7,799,076 B2 * | 9/2010 | Sybert et al. | 623/13.17 |
| 2002/0072806 A1 * | 6/2002 | Buskirk et al. | 623/23.51 |
| 2005/0203622 A1 | 9/2005 | Steiner et al. | |

FOREIGN PATENT DOCUMENTS

| | | |
|---|---|---|
| WO | WO 94/26892 | 11/1994 |
| WO | WO 94/26893 | 11/1994 |
| WO | WO 98/44965 | 10/1998 |
| WO | WO 99/21515 | 5/1999 |
| WO | WO 99/39757 | 8/1999 |
| WO | WO 00/59388 | 10/2000 |

OTHER PUBLICATIONS

Lewandrowski, et al., "Kinetics of cortical bone demineralization: Controlled demineralization-a new method for modifying cortical bone allografts", *Journal of Biomedical Materials Research*, vol. 31, pp. 365-372 (1996).

Mohamed, "Three-dimensional Textiles", *American Scientist*, vol. 78, pp. 530-541 (Nov.-Dec. 1990).

Reddi, et al., "Biochemical Sequences in the Transformation of Normal Fibroblasts in Adolescent Rats", *Proc. Nat. Acad. Sci*, USA, vol. 69, No. 6, pp. 1601-1605 (Jun. 1972).

Shaw, "KNOTS—Useful & Ornamental, Bonanza Books", New York (1983).

* cited by examiner

BIOCOMPATIBLE OSTEOGENIC BAND FOR REPAIR OF SPINAL DISORDERS

CROSS-REFERENCE TO RELATED APPLICATIONS

This application is a Continuation Application of U.S. application Ser. No. 12/193,534, filed Aug. 18, 2008, now issued as U.S. Pat. No. 7,799,076, which is a Continuation Application of U.S. application Ser. No. 10/850,149, filed on May 20, 2004, now issued as U.S. Pat. No. 7,413,576, which is a Continuation Application of U.S. application Ser. No. 09/733,327, filed on Dec. 8, 2000, now issued as U.S. Pat. No. 6,752,831, the contents of all of which are incorporated herein by reference in their entirety.

BACKGROUND OF THE INVENTION

1. Technical Field

The present invention relates to methods for repairing spinal disorders. More particularly, the present invention relates to a method of repairing spinal disorders, especially those requiring spinal fusion, using a biocompatible osteogenic band which induces new bone growth formation at the site of implantation.

2. Description of the Related Art

The vertebral column (spine) is a biomechanical structure composed of a series of joints known as motion segment units. Each motion segment unit includes two adjacent vertebrae and their facet capsules, the intervertebral disc, and connecting ligament tissue. The spine is divided into four major regions which include the cervical, thoracic, lumbar and sacral regions and functions to protect the spinal cord and nerve roots, and provide support to the body. The intervertebral disc is located between the two endplates of adjacent vertebrae and is composed of the nucleus pulposus (a gel-like ball located at the center of the disc) and annulus fibrous (collagen fibers surrounding the nucleus pulposus). The intervertebral disc stabilizes the spine, and provides the spine with resiliency and the ability to withstand compression, rotation and bending strain. The facet capsules are bony elements which aid in the support of compressive loads and resist torsional motion. Ligaments connected to the spine support loads in tension and help provide spinal stability by limiting excessive range of motion and absorbing energy applied due to trauma.

Various types of spinal disorders are known and include kyphosis (backward curvature of the spine), spondylolysis, spondylolisthesis (forward displacement of a lumbar vertebrae), scoliosis (abnormal curvature of the spine) and disorders involving ruptured, slipped, damaged and diseased discs, damaged vertebrae, and the like. Patients suffering from the aforementioned disorders typically experience severe pain, numbness, decreased mobility, muscle weakness and nerve damage.

Spinal fusion is frequently used as a treatment for such disorders and is achieved by formation of a bony bridge between adjacent motion segments eliminating the intervertebral joint. Spinal fusion can be accomplished within the disc space, anteriorly between adjacent vertebral bodies and/or posteriorly between consecutive processes, e.g., transverse processes, laminae or other posterior elements of the vertebrae.

One frequently used spinal fusion technique involves removal of the intervertebral disc and insertion of an anterior supporting structure, e.g., bone grafts, bone substitutes, plugs, bone dowels, cages, and the like, into the intervertebral disc space to prevent collapse of the disc space and promote fusion of the adjacent vertebrae. To ensure proper growth and fusion between the affected adjacent vertebrae, the posterior side of the spine is frequently stabilized by utilizing a rigid metallic implant, e.g., a plate, rod, wire or strip, which spans the adjacent vertebrae to re-create a load distribution similar to that of the intact spine. These metallic implants are commonly referred to throughout the relevant scientific and medical literature as "tension bands."

The use of such metallic implants to stabilize the spine and facilitate fusion presents several disadvantages. One disadvantage encountered utilizing such metallic implants is that once fusion occurs the metallic implant becomes superfluous and remains as a permanent foreign fixture. As the metallic implant loosens enough to allow relative motion, particulates are generated as wear debris. This wear debris then has the potential to cause a foreign body response. Metallic implants are also subject to fatigue failure due to repeated cyclic loading. An implant that is remodeled, and then repaired as it later becomes damaged, will not fail due to fatigue. Another disadvantage is that the implanted metallic implant itself possesses ferromagnetic properties and thus prevents the use of post-operative plain film X-rays, MRI or CT scan imaging due to scattering of the image. Yet another disadvantage is that when such metallic implants are placed over bone tissue, any tension load placed on the spine is transmitted to the implant rather than the bone tissue, thereby "stress shielding" the bone. Over a period of time, bone tissue that is shielded from tension loads is removed by the body thereby weakening the structure of the bone. Accordingly, removal of the implant by a second operation may be required to prevent loss of bone tissue caused by stress shielding.

In view of the aforementioned limitations posed by using rigid metallic implants to stabilize the spine and facilitate fusion, there is a need to provide a method of treating spinal disorders that will provide for the fusion of bone at the implant site, thereby providing a graft that will not fail mechanically or cause rejection in the patient, and will not require removal in a subsequent operation.

Therefore, it is an object of the present invention to provide a method of stabilizing the spine which overcomes the limitations of rigid metallic implants.

It is a further object of the present invention to provide a method of stabilizing the spine with a device that is non-antigenic and will not be rejected by the host.

It is a further object of the present invention to provide a method of stabilizing the spine with a device that is biocompatible and will not require removal in a subsequent operation.

It is a further object of the present invention to provide a method of stabilizing the spine with a device that is osteogenic and that adequately supports tension loads.

It is a further object of the present invention to provide a method of stabilizing the spine with a device that will avoid stress shielding.

It is a further object of the present invention to provide a method of stabilizing the spine with a device that supports fusion between adjacent vertebrae.

It is a further object of the present invention to provide a method of stabilizing the spine with a device which can be utilized in conjunction with an anterior supporting structure.

Other objects of the invention will be apparent to those skilled in the art in view of the above objects and the foregoing specification.

SUMMARY OF THE INVENTION

These and further objects of the invention are obtained by a method for repairing a spinal disorder which comprises affixing a biocompatible osteogenic band to two or more vertebrae of a spine to maintain the two or more vertebrae under tension, wherein the band is fabricated in whole or in part from biocompatible fibers of a native, biosynthetic, or synthetic polymeric, connective tissue or plant connective tissue-like containing component that is osteoinductive or has been treated to be osteoinductive. The osteogenic material can include bone, tendon, ligament, silk, collagen, elastin, reticulin, cellulose, alginic acid, chitosan, small intestine submucosa, biocompatible polymers or combination thereof which has been rendered osteogenic by one or more procedures described hereinbelow. A suitable material is disclosed in the U.S. Provisional Application No. 60/254,339, filed Dec. 8, 2000, and subsequently filed as a Non-Provisional application Ser. No. 10/433,359 on Dec. 3, 2001, the contents of both of which are incorporated by reference herein.

A method for repairing a spinal disorder is also provided which comprises inserting an anterior supporting structure into a disc space between adjacent vertebrae of a spine and affixing a biocompatible osteogenic band to two or more vertebrae of the spine to maintain the two or more vertebrae under tension.

Affixation of the foregoing biocompatible osteogenic band to the spine leads to new bone ingrowth by one or more biological mechanisms such as osteogenesis, osteoconduction and/or osteoinduction or by one or more physical mechanisms such as providing a support for new bone growth. The expression "osteogenic material" as utilized herein shall therefore be understood as referring to a material which will participate in the process of new bone growth regardless of the mechanism(s) involved. The osteogenic material can be obtained from sources which are not in themselves osteogenic but are rendered osteogenic by incorporation and/or associating therewith one or more osteogenic components. Accordingly, unlike metallic implants, the biocompatible osteogenic band of this invention contributes to the development of a fusion preferably across vertebral bodies of the posterior spine and aids in the repair and stabilization of the spine.

Another advantage of the present invention is that the biocompatible osteogenic band preferably provides posterior tensile loading, thereby recreating a load distribution similar to that of the intact spine.

Another advantage of the present invention is that, unlike conventional metallic implants, the biocompatible osteogenic band is sufficiently flexible to allow affixation to a vertebral site yet sufficiently strong, tough and inextensile to withstand applied excessive force. Because the material is osteogenic, new bone is formed around and within the implant and the biocompatible osteogenic band is incorporated with new bone tissue via the process of remodeling. Accordingly, unlike a metallic implant which persists long after its useful life, it is not necessary to remove the biocompatible osteogenic band in a subsequent operation.

Another advantage of the present invention is that, unlike conventional metallic implants, the biocompatible osteogenic band will not stress shield the bone. In addition, unlike metallic implants, the biocompatible osteogenic band does not interfere with the use of post-operative plain film X-rays, or MRI and CT scans.

Other advantages of the present invention will become apparent to one skilled in the art from the following written description and accompanying figures.

BRIEF DESCRIPTION OF THE DRAWINGS

FIGS. 1A-1C are diagrammatic representations of tension bands fabricated from elongated sections of bone. In FIG. 1A the elongated section of bone is cut or machined to provide end and middle portions possessing the same width. In FIGS. 1B-1C the elongated section of bone is cut or machined to provide end portions possessing a greater width than the middle portion, and end portions possessing round (FIG. 1B) and square (FIG. 1C) configurations that taper off. FIG. 1A also schematically depicts an elongated section of bone cut or machined to exhibit threads on one end and an attachment hole at the other end. FIGS. 1B-1C also schematically depict an elongated section of bone cut or machined to exhibit an attachment hole on each end.

DESCRIPTION OF THE PREFERRED EMBODIMENTS

The present invention is directed to a novel method of repairing a spinal disorder which involves affixing a biocompatible osteogenic band to two or more vertebrae of the spine, preferably the posterior aspect of the spine, to maintain the two or more vertebrae under tension. The foregoing biocompatible osteogenic band can be used alone or in conjunction with other classical approaches to repair a spinal disorder, such as the use of an anterior supporting structure as described in more detail below. Spinal disorders which can be repaired by the method described herein include, but are not limited to, ruptured and damaged discs, degenerative disc disease, spondylolysis, spondylolisthesis, scoliosis, spinal injuries caused by trauma or surgery, etc.

The biocompatible osteogenic band is fabricated in whole or in part from various materials, particularly connective type biological material obtained from human and animal tissues, plants, and insects which include, but are not limited to, e.g., bone, tendon, ligament, silk, collagen, elastin, reticulin, cellulose, alginic acid, chitosan, small intestine submucosa or combinations thereof. The biological material can be autogenic, allogenic or xenogenic in origin. The biological material can also be obtained from microorganisms, particularly genetically engineered microorganisms such as yeast and bacteria and genetically engineered eucaryotic cell cultures such as Chinese hamster ovary cell lines, HeLa cells, etc. For example, U.S. Pat. Nos. 5,243,038 and 5,989,894, each incorporated herein by reference, describes the expression of spider silk protein, collagen proteins, keratins, etc., using genetically engineered microorganisms and eucaryotic cell lines.

The biocompatible osteogenic band can also be fabricated in whole or in part from synthetic biocompatible polymers that have been rendered osteogenic as described below. Suitable biocompatible polymers would include, for example, poly(lactide), polyglycolides, poly(epsilon-caprolactone), etc.

Figures 1A, 1B:
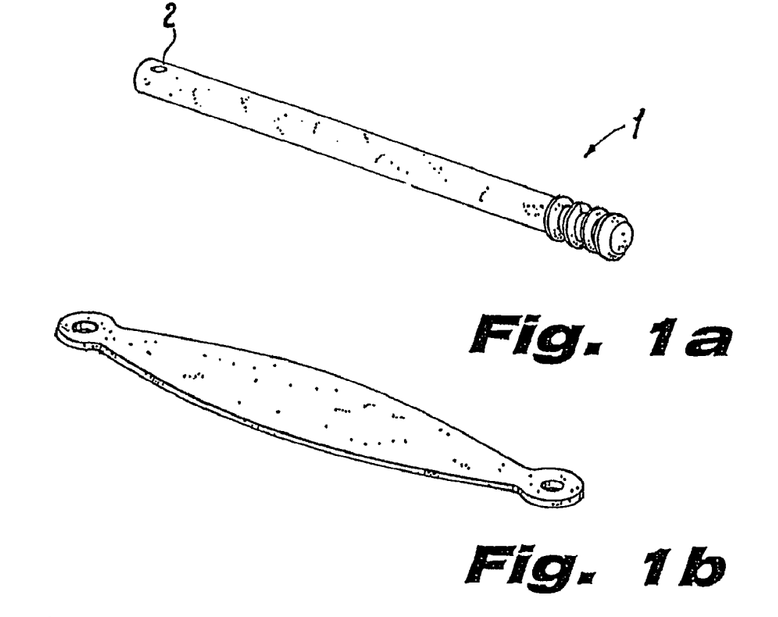
Figure 1C:
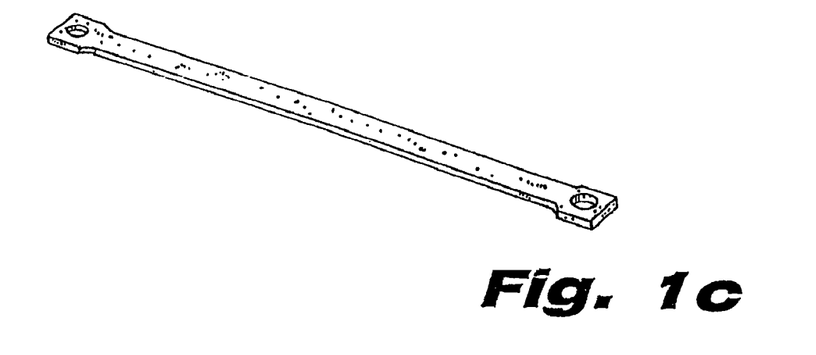

To function effectively in repairing the spine, the biocompatible osteogenic band, particularly when fabricated in whole or in part from biological material such as bone, tendon, ligament, and small intestine submucosa tissue, is first processed to clean the tissue of blood and debris, and to sterilize the tissue by routine procedures as described below. The processed tissue is then fashioned into one or more elongated sections. The dimensions of an elongated section are selected so that the material possesses sufficient length to span and be affixed to the affected vertebrae, and also possesses sufficient width and thickness to impart toughness, flexibility and strength to the section. One skilled in the art will recognize that the elongated section of material, particularly an elongated section of bone, can be further cut or machined by any convenient method into a variety of different shapes as shown in FIGS. 1A-1C. For example, FIG. 1A schematically depicts one embodiment of an elongated section of bone which is further cut or machined to provide end and middle portions possessing the same width. FIGS. 1B-1C schematically depict other embodiments wherein an elongated section of bone is further cut or machined to provide end portions possessing a greater width than the middle portion, and end portions having a round (FIG. 1B) or square (FIG. 1C) configuration that tapers off. Likewise, the processed tissue, when fibrous or prepared as thin sections, can be woven or knitted to form a cloth-like material useful as the biocompatible osteogenic band herein. Another configuration of a biocompatible osteogenic band useful in the practice of the invention herein would be a composite structure such as a central core of demineralized monolithic bone surrounded by a weave of bioabsorbable fibers. The anchoring of the implant would be assisted by the bioabsorbable fibers while the demineralized monolithic bone core would provide osteogenic characteristics. The term "monolithic" as utilized herein refers to a unitary portion of bone having a total surface area of at least 40 mm$^3$.

It is further recognized that the end portions of an elongated section can be cut or machined to include threads, grooves, driver head, fasteners, rivets, screws, bolts, pins, etc., to aid in affixing each end portion of the elongated section to the vertebrae. FIG. 1A schematically depicts one embodiment of an elongated section of bone which is machined to exhibit threads 1 at one end and an attachment hole 2 at the other end. FIGS. 1B-1C schematically depict other embodiments of an elongated section of bone which is machined at both ends to exhibit an attachment hole 2.

Accordingly, the overall dimensions of the elongated sections of the biocompatible osteogenic band can vary widely depending on the distance between affected vertebrae, the site, and the method of affixation. Typically, the dimensions of the biocompatible osteogenic band will range from about 1 cm to about 1 meter in length, preferably from about 3 cm to about 8 cm in length, from about 2 mm to about 30 mm in thickness, preferably from about 2 mm to about 10 mm in thickness, and from about 2 mm to about 30 mm in width, preferably from about 2 mm to about 10 mm in width.

While fully mineralized bone, tendon, ligament, silk, collagen, elastin, reticulin, cellulose, alginic acid, chitosan, small intestine submucosa and biocompatible polymers in themselves are not osteogenic, such materials can be rendered osteogenic by subjecting the material to various procedures and/or incorporating in, or associating with, the material various osteogenic components. For example, the mineral content of bone tissue can be reduced by demineralization, a process which results in the removal of the inorganic components of the bone, largely hydroxyapatite, which gives bone its characteristic rigidity and structural properties. The resultant demineralized bone is flexible and osteogenic. Bone, tendon, ligament, silk, collagen, elastin, reticulin, cellulose, alginic acid, chitosan, small intestine submucosa and biocompatible polymers can be rendered osteogenic by association with, or incorporation of, various osteogenic components which include, but are not limited to, growth factors such as bone-derived growth factor, bone morphogenic proteins, osteogenic proteins such as OP-1, hormones, growth hormone, platelet derived growth factor (PDGF), insulin-like growth factors (IGF-1)(IGF-2), DNA encoding various therapeutic agents such as growth factors and hormones, gene activated matrix, i.e., a matrix containing DNA encoding therapeutic proteins utilized to promote cell growth, which in turn, promote DNA transfer into repair cells, demineralized bone in the form of particles, powder, gel, liquid, etc., ceramic powders of calcium phosphate and/or apatite (hydroxyapatite) and bioglass. Bone morphogenic proteins can be obtained from, e.g., Genetics Institute, Inc. (Cambridge, Mass.) and Stryker Corporation (Kalamazoo, Mich.), and may also be prepared by one skilled in the art as described, e.g., in U.S. Pat. Nos. 5,187,076, 5,366,875, 4,877,864, 5,108,922, 5,116,738, 5,013,649, 5,106,748, WO93/00432, WO94/26893 and WO94/26892, each incorporated herein by reference.

All osteogenic components are contemplated whether they are obtained as above or isolated from bone. Methods for isolating bone morphogenic protein from bone are described, e.g., in U.S. Pat. No. 4,294,753, incorporated herein by reference. Methods of preparing demineralized bone powder, demineralized bone particles, and demineralized bone in the form of a liquid, and demineralized bone in the form of a gel are well known in the art as described, e.g., in U.S. Pat. Nos. 5,314,476, 5,507,813, 5,073,373, and 5,405,390, respectively, each incorporated herein by reference. Methods of preparing osteogenic proteins, such as OP-1 are described, e.g., in U.S. Pat. No. 6,048,964, incorporated herein by reference. Methods of transferring DNA encoding therapeutic proteins into repair cells utilizing gene activated matrix are described, e.g., in U.S. Pat. No. 5,962,427 incorporated herein by reference. Methods of preparing ceramic powders of calcium phosphate and/or hydroxyapatite are described, e.g., in U.S. Pat. Nos. 4,202,055 and 4,713,076, each incorporated herein by reference. Methods of preparing bioglasses are described, e.g., in WO 98/44965, incorporated herein by reference. Suitable methods of incorporation or association of such osteogenic factors include coating, immersion saturation, dispersing, packing, spraying, e.g., plasma spraying, injecting into the bone tissue, etc.

When the biocompatible osteogenic band is fabricated from bone, the bone is preferably chosen from a cortical bone, such as from the femur, tibia, fibula, radius or ulna. The bone can be obtained from an autogeneic, allogeneic or xenogeneic source, and is preferably obtained from an autogeneic or allogeneic source.

In one embodiment, the biocompatible osteogenic band comprises at least one elongated section of bone and preferably a plurality of elongated sections of bone. Typically, the bone is obtained from a suitable vertebrate and processed by conventional techniques to remove blood and lipid from the bone. The bone can then be cut into elongated sections by techniques which are well known in the art, e.g., longitudinally cutting an entire bone section or relatively large portion of bone into elongated sections using a band saw or a diamond-bladed saw, or milling the surface of an entire bone or relatively large portion of bone. Alternatively, the bone can be cut by making transverse cuts to prepare a bone section of the appropriate length, followed by longitudinal cuts using a band saw or a diamond cut saw. As stated above, elongated section(s) of bone can be further cut or machined into a variety of different shapes. In overall appearance the elongated sections of bone can be described as narrow or thick strips, segments, sheets, rods, struts, etc. The elongated bone sections can be further processed to remove residual blood and lipid residue.

Prior to or subsequent to cutting or milling of the bone into elongated sections, the bone section(s) are preferably demineralized to reduce the inorganic content of the bone. The mineral content of bone can be removed to varying degrees. The term "fully demineralized" as it applies to an elongated bone section refers to a bone section possessing less than about 8, preferably less than 1, weight percent of its original inorganic mineral content. The term "partially demineralized" as it applies to an elongated bone section means that the elongated bone section possesses from about 8 to about 90 weight percent of its original inorganic mineral content. The term "superficially demineralized" as it applies to an elongated bone section refers to a bone section possessing at least 90 weight percent of their original inorganic mineral content. The unmodified term "demineralized" as it applies to an elongated bone section is intended to cover any one or combination of the foregoing types of demineralized, elongated bone sections. The use of superficially, partially or fully demineralized bone is beneficial since it exhibits osteogenic activity unlike fully mineralized bone.

Demineralization of the elongated bone sections can be conducted using conventional procedures that are well known in the art, e.g., subjecting the bone section to strong acids such as hydrochloric acid as described, e.g., in Reddi et al., Proc. Nat. Acad. Sci. 69:1601-5 (1972), incorporated herein by reference. The extent of demineralization is a function of the strength of the acid solution, the shape of the bone and the duration of the demineralization treatment. Reference in this regard may be made to Lewandrowski et al., J. Biomed. Materials Res. 31:365-372 (1996), incorporated herein by reference.

In a preferred bone demineralization procedure, the elongated bone section or sections are subjected to a defatting/disinfecting step which is followed by an acid demineralization step. A preferred defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to about 90 weight percent of defatting agent such as alcohol) should be present in the defatting/disinfecting solution to produce optimal lipid removal and disinfection within the shortest period of time. The preferred concentration range of the defatting solution is from about 60 to 85 weight percent alcohol and most preferably about 70 weight percent alcohol. Following defatting, the bone is immersed in acid over time to effect its demineralization. Acids which can be employed in this step include inorganic acids such as hydrochloric acid and organic acids such as peracetic acid. Generally, the concentration of inorganic acid utilized to achieve demineralization is from about 0.1N to about 2N and more preferably from about 0.2 N to about 1.0 N. The time of exposure to the acid is increased for lower acid concentrations and decreased for the higher acid concentrations. After acid treatment, the elongated bone section(s) are rinsed with sterile water for injection, buffered with a buffering agent to a final predetermined pH and then finally rinsed with water for injection to remove residual amounts of acid and buffering agent or washed with water to remove residual acid and thereby raise the pH.

Figure 2:
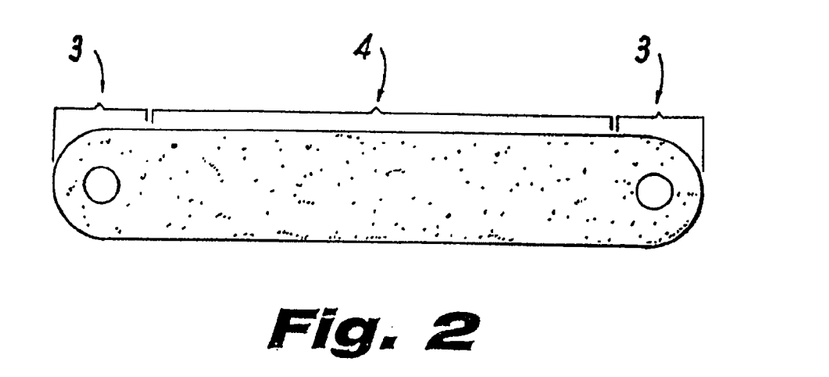
FIG. 2 is a diagrammatic representation of a segmentally demineralized bone section wherein the end portions are fully mineralized (solid lines) and the middle portion is partially demineralized (dots).

In a particularly useful embodiment, the elongated bone section or sections are segmentally demineralized. The term "segmentally demineralized" as applied to the elongated bone section(s) refers to elongated bone section(s) wherein one or both end portions of the bone section(s) remain fully mineralized or are surface demineralized and the middle portion of the bone section(s) is fully or partially demineralized. The extent of demineralization of the segmentally demineralized bone section is generally up to about 10 percent for one or both end portions and at least 50 percent for the middle portion. The fully or partially demineralized middle portion imparts to the elongated bone section(s) sufficient flexibility and strength to allow that portion of the bone section to bear the load of the posterior spine, while each end portion of the elongated bone section(s) is securely affixed to the vertebral body at the sites of affixation. FIG. 2 schematically depicts a segmentally demineralized bone section possessing fully mineralized end portions 3 and a partially demineralized middle portion 4. The segmentally demineralized bone section can be prepared by procedures known in the art as described, e.g., in WO 99/21515 and U.S. Pat. No. 6,090,998, each incorporated herein by reference. For example, the end portions of the bone section(s) can remain fully mineralized by protecting that portion with any type of protective device or composition such as plastic wrap, paraffin, a rubber or latex covering, and the like. The remaining middle portion of the bone section(s) are then demineralized according to methods known in the art, e.g., use of hydrochloric acid solution as described above. As another example, the segmentally demineralized bone section can be prepared by placing collar shields around the end portions of the bone section and allowing the acid solution to flow over the middle portion of the bone section. Preferably, the point of contact of the hydrochloric acid solution with the middle portion of the bone section(s) is varied over the duration of the demineralization process to produce a gradual transition from a fully mineralized end portion to a fully or partially demineralized middle portion.

Alternatively, the end portions of the elongated bone section(s) can be surface demineralized by any convenient method. For example, entire bone section(s) can be subjected to demineralization conditions for a desired period of time sufficient to demineralize only the surface of the elongated bone section(s). The end portions of the bone section(s) can then be washed and rinsed with sterile water, and covered with a protective device as described above. Subsequently, the middle portion of the elongated bone section(s) can be subjected to further demineralization.

The demineralized, elongated bone section(s) can be used immediately by affixing the bone section(s) to the region of the spine in need of repair or it can be stored under aseptic conditions, e.g., freeze dried, and then rehydrated prior to use. The bone section(s) can be further cut or sized to conform to the site being repaired.

If desired, elongated bone section(s) can be treated with chemical agents, such as hydrogen peroxide and with enzymes to modify the mechanical properties and chemical composition of the bone structure. In addition, the bone section(s) can be treated with chemical agents, e.g., glutaraldehyde, to reduce the antigenicity of the section(s).

Figure 3A:
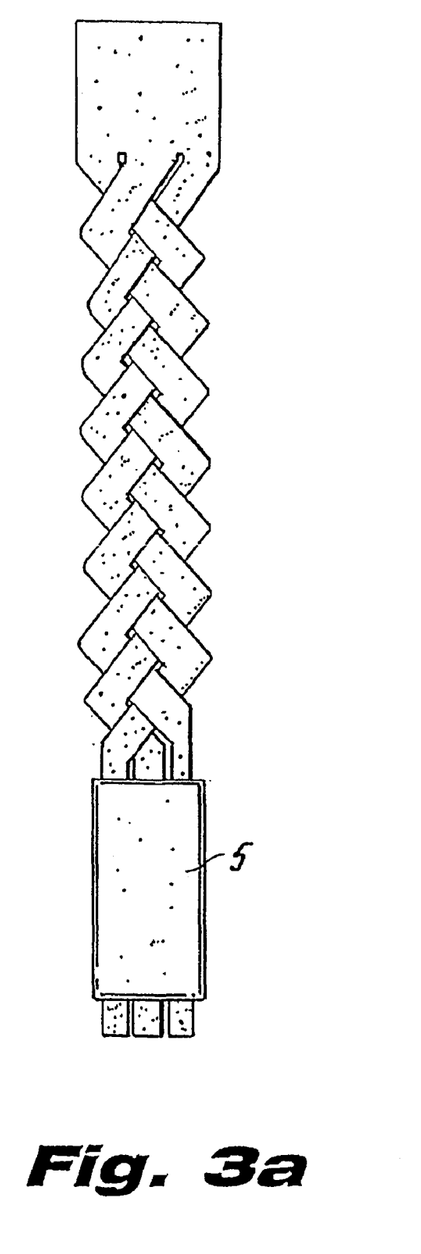
FIGS. 3A-E are diagrammatic representations of demineralized bone strips arranged into various structures.
Figure 3B:
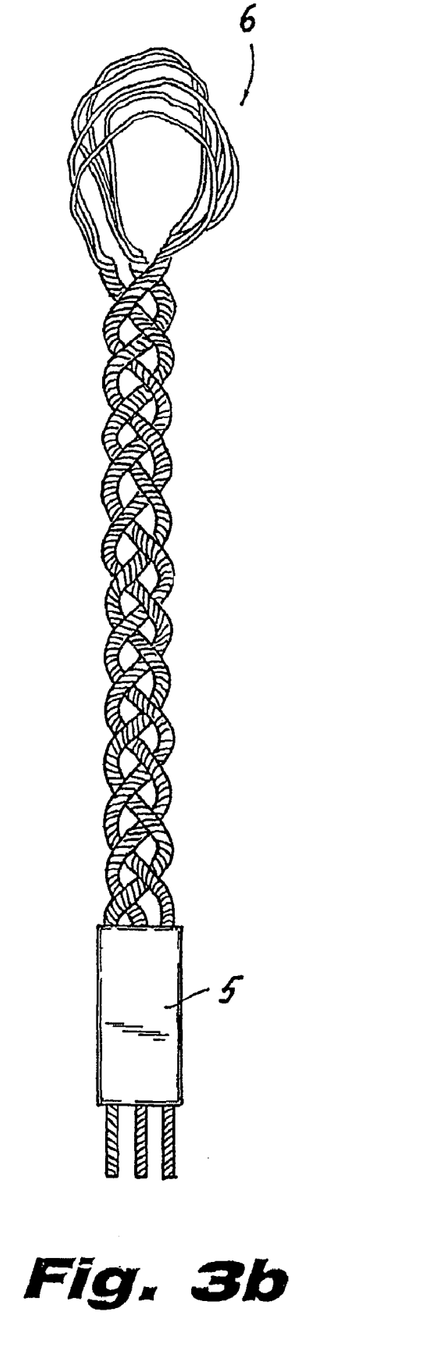
Figure 3C:
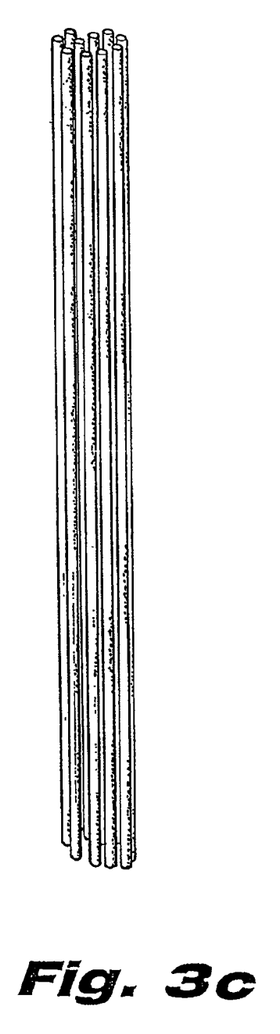
Figure 3D:
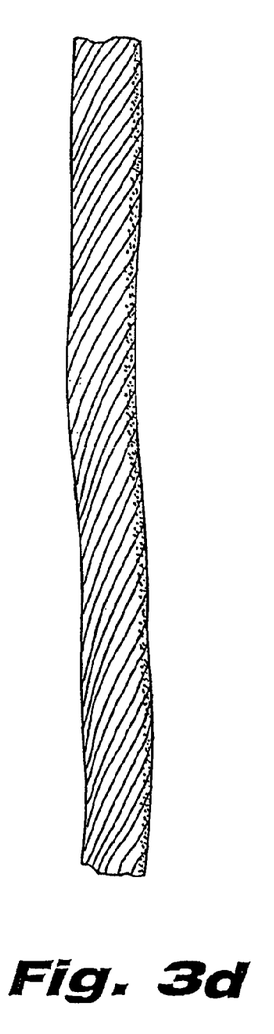
Figure 3E:
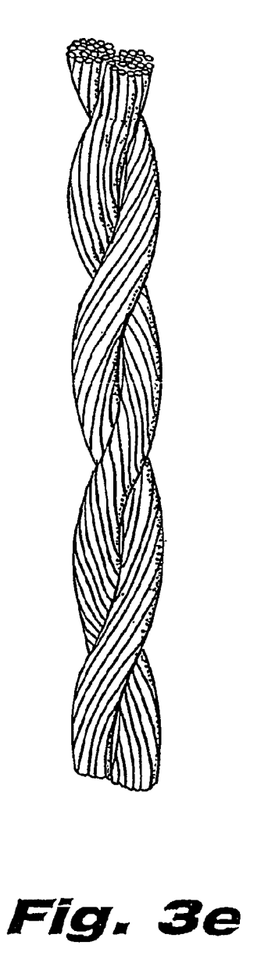

The flexible demineralized bone sections can be arranged to form a variety of different structures as shown in FIGS. 3A-3E. For example, three or more demineralized, elongated bone sections can be woven together to form a braid (FIG. 3A). A plurality of demineralized, elongated bone sections can be aligned longitudinally and twisted together to form a multi-bone section bundle, which can then be used to form a multi-bone section braid of three or more bundles (FIG. 3B). The demineralized bone sections can be longitudinally aligned to form a single untwisted bundle (FIG. 3C) or twisted to form a single-twisted bundle (FIG. 3D). Two or more bundles of multi-bone sections can be wrapped around each other to form a two or more bundle helix (FIG. 3E). The end of the tension band is sealed into a mesh tube 5 made from a bioabsorbable or non-bioabsorbable polymer.

In one embodiment used to prepare a tension band of braided sections of demineralized bone (FIG. 3B), demineralized bone sections (approximately 6 bone sections) are combined longitudinally into three small bundles, each having from about 1 to about 3 bone sections. These bundles are first braided at the mid-length and then folded at the braided region to form a turn and a loop 6. The six bundles are then recombined to form three bundles which are then braided.

Various methods of braiding and types of braids are also described, e.g., by Shaw, KNOTS—Useful & Ornamental, Bonanza Books, New York (1983), incorporated herein by reference. The ends of the braided demineralized bone section can be glued together using a fixation agent to prevent the braided ends from unraveling or-sealed into a mesh tube 5 as described above.

In another embodiment, demineralized bone strips can be cut from sheets composed of elongated bone particles, commercially available as GRAFTON® Flex (Osteotech, Eatontown, N.J.) as described, e.g., in U.S. Pat. No. 5,507,813, incorporated herein by reference or as disclosed in U.S. patent application Ser. No. 09/610,026, now issued under U.S. Pat. No. 6,863,694, incorporated herein by reference.

To increase the mechanical strength of bone strips fabricated from bone particles chemical linkages can be formed between adjacent bone particles. Such chemical linkages are obtained by partial or superficial demineralization of the bone to expose collagen on adjacent bone particles and forming collagen-collagen bonds, as described, e.g., in U.S. patent application Ser. No. 09/020,205, now issued under U.S. Pat. No. 6,123,731, incorporated herein by reference.

These chemical linkages can be formed employing a variety of known methods including chemical reaction, the application of energy such as radiant energy, which includes irradiation by UV light or microwave energy, drying and/or heating and dye-mediated photo-oxidation; dehydrothermal treatment in which water is slowly removed while the bone tissue is subjected to a vacuum; and, enzymatic treatment to form chemical linkages at any collagen-collagen interface. The preferred method of forming chemical linkages is by chemical reaction.

Chemical crosslinking agents include those that contain bifunctional or multifunctional reactive groups, and which react with functional groups on amino acids such as epsilon-amine functional group of lysine or hydroxy-lysine, or the carboxyl functional groups of aspartic and glutamic acids. By reacting with multiple functional groups on the same or different collagen molecules, the reacting chemical crosslinking agent forms a reinforcing cross-bridge.

Suitable chemical crosslinking agents include: mono- and dialdehydes, including glutaraldehyde and formaldehyde; polyepoxy compounds such as glycerol polyglycidal ethers, polyethylene glycol diglycidal ethers and other polyepoxy and diepoxy glycidal ethers; tanning agents including polyvalent metallic oxides such as titanium dioxide, chromium dioxide, aluminum dioxide, zirconium salt, as well as organic tannins and other phenolic oxides derived from plants; chemicals for esterification of carboxyl groups followed by reaction with hydrazide to form activated acyl azide functionalities in the collagen; dicyclohexyl carbodiimide and its derivatives as well as other heterobifunctional crosslinking agents; hexamethylene diisocyanate; sugars, including glucose, will also cross-link collagen.

Glutaraldehyde cross linked biomaterials have a tendency to over-calcify in the body. In this situation, should it be deemed necessary, calcification-controlling agents can be used with aldehyde crosslinking agents. These calcification-controlling agents include: dimethyl sulfoxide (DMSO), surfactants, diphosphonates, amino oleic acid, and metallic ions, for example ions of iron and aluminum. The concentrations of these calcification-controlling agents can be determined by routine experimentation by those skilled in the art.

Chemical crosslinking involves exposing the bone particles presenting surface-exposed collagen to the chemical crosslinking agent, either by placing the elements in a solution of the chemical crosslinking agent, or by exposing them to the vapors of the chemical crosslinking agent under conditions appropriate for the particular type of crosslinking reaction. Such conditions include: an appropriate pH and temperature, and for times ranging from minutes to days, depending upon the level of crosslinking desired, and the activity of the chemical crosslinking agent. The bone particles are then washed to remove all leachable traces of the chemical.

When enzymatic treatment is employed, useful enzymes include those known in the art which are capable of catalyzing crosslinking reactions on proteins or peptides, preferably collagen molecules, e.g., transglutaminase as described in Jurgensen et al., *The Journal of Bone and Joint Surgery*, 79-A (2), 185-193 (1997), herein incorporated by reference.

Formation of chemical linkages can also be accomplished by the application of energy. One way to form chemical linkages by application of energy is to use methods known to form highly reactive oxygen ions generated from atmospheric gas, which in turn, promote oxygen cross-linkage between surface-exposed collagen. Such methods include using energy in the form of ultraviolet light, microwave energy and the like. Another method utilizing the application of energy is a process known as dye-mediated photo-oxidation in which a chemical dye under the action of visible light is used to cross-link surface-exposed collagen.

Another method for the formation of chemical linkages is by dehydrothermal treatment which uses combined heat and the slow removal of water, preferably under vacuum, to achieve crosslinking of the bone-derived elements. The process involves chemically combining a hydroxy group from a functional group of one collagen molecule and a hydrogen ion from a functional group of another collagen molecule reacting to form water which is then removed resulting in the formation of a bond between the collagen molecules.

While cross-linking will improve the strength of the material, it may reduce the osteoinductivity of the material. Therefore, when desirable, a suitable inductive agent, e.g., BMP, DBM, etc., can be employed to improve the osteoinductive properties of the tanned or cross-linked materials.

The mechanical strength of bone strips composed of the elongated bone particles can also be increased by braiding the bone strips as described above.

Medically/surgically useful substances which promote or accelerate new bone growth or bone healing can be incorporated in, or associated with, the mineralized or demineralized elongated bone section(s). Useful substances of this kind which can be incorporated into the bone section(s) include, e.g., collagen, insoluble collagen derivatives, etc., and soluble solids and/or liquids dissolved therein, e.g., antiviral agents, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin, and gentamicin, etc.; biocidal/biostatic sugars such as dextran, glucose, etc.; amino acids; peptides; vitamins; inorganic elements; co-factors for protein synthesis; hormones; endocrine tissue or tissue fragments, synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells; natural extracts; genetically engineered living cells or otherwise modified living cells; tissue transplants; demineralized bone powder (or "demineralized bone matrix" as it may also be referred to); DNA delivered by plasmid or viral vectors; autogenous tissues such as blood, serum, soft tissue, bone marrow, etc.; bioadhesives; bone morphogenic proteins; osteoinductive factor; fibronectin; transforming growth factor-beta; endothelial cell growth factor; cementum attachment extracts; ketaserin; insulin-like growth factors (IGF-1)(IGF-2); platelet derived growth factors (PDGF); epidermal growth factor (EGF); interleukin; human alphathrombin; fibroblast growth factors; periodontal ligament chemotactic factor; hormones, human growth hormone; animal growth hormone; growth hormones such as somatotropin; bone digesters; antitumor agents; immuno-suppressants; permeation enhancers, e.g., fatty acid ester such as laureate, myristate and stearate monoesters of polyethylene glycol, enamine derivatives, alpha-keto aldehydes, etc.; and, nucleic acids. Preferred biomedically/surgically useful substances are bone morphogenic proteins and DNA delivered by plasmid or viral vector. Suitable methods of incorporation include coating, immersion saturation, packing, co-lyophilization wherein the substance is placed on the bone graft and lyophilized, spraying, injecting into the bone tissue, etc. The amounts of medically/surgically useful substances utilized can vary widely with optimum levels being readily determined in a specific case by routine experimentation.

The biocompatible osteogenic band can also be fabricated in whole or in part from tendon tissue. Tendon tissue itself is not osteogenic, but it can be made osteogenic by incorporating in, or associating with, the tendon tissue various osteogenic components as described above. Tendon tissue useful for fabricating the tension band includes, but is not limited to, fascia lata, semitendinosus, achilles tendon and patella tendon tissue. The tendon tissue may be obtained from an autogeneic, allogeneic or a xenogeneic source, and preferably is obtained from an autogeneic or allogeneic source. The tendon can be excised and utilized in its entirety or alternatively, is cut into at least one elongated section or a plurality of elongated sections by methods well known to those skilled in the art. Reduction of the antigenicity of allogeneic and xenogeneic tendon tissue can be achieved by treating the tissue with various chemical agents, e.g., extraction agents such as monoglycerides, diglycerides, triglycerides, dimethyl formamide, etc., as described, e.g., in U.S. Pat. No. 5,507,810, incorporated herein by reference. Medically/surgically useful substances as described above can also be incorporated in or associated with the tendon tissue as described above with respect to tension bands fabricated from bone.

The biocompatible osteogenic band can also be fabricated in whole or in part from ligament tissue. Ligament tissue itself is not osteogenic, but can be made osteogenic by the incorporation of various osteogenic components as described above. Ligament tissue which is useful in fabricating the tension band can comprise an entire excised ligament, or at least one elongated section of ligament or a plurality of elongated sections of ligament. Ligament tissue can be obtained from an autogeneic, allogeneic or xenogeneic source, and preferably is obtained from an autogeneic or allogeneic source. The whole ligament can be excised from the source by techniques well known in the art and utilized in its entirety or cut longitudinally into an elongated section or sections of ligament using conventional techniques known in the art. The whole ligament or section(s) of ligament can be further cut to the desired size to conform to the region of the posterior spine being repaired. Ligament tissue obtained from an allogeneic or xenogeneic source can be further treated by various agents to reduce its antigenicity or with various medically/surgically useful substances as described above.

When utilizing a plurality of ligament sections, such sections can be arranged to form a variety of structures as described above for elongated bone sections. For example, ligament sections can be twisted to form a bundle which can be then be utilized to form a braid of three or more bundles. A plurality of ligament sections can be aligned longitudinally to form an untwisted bundle, or two or more bundles of ligament sections can be wrapped about each other to form a helix. Preferably, the plurality of ligaments is woven into a braid.

The biocompatible osteogenic band can also be fabricated from collagen tissue which can be obtained from any autogeneic, allogeneic, or xenogeneic source, and preferably from an autogeneic or allogeneic source. Collageneous tissue sources can include, but are not limited to, skin, tendon, intestine and dura mater, obtained from animals, transgenic animals, and humans. Collageneous tissue can also be obtained by genetically engineering microorganisms to express collagen as described, e.g., in aforementioned U.S. Pat. No. 5,243,038. Procedures for obtaining and purifying collagen are well known in the art and typically involve acid or enzyme extraction as described, e.g., in U.S. Pat. No. 5,263,984, incorporated herein by reference. Collagen is also commercially available (Pentapharm Ltd., Basel, Switzerland). The purified collagen is then subjected to further processing to obtain collagen fibers or collagen threads, which can optionally be treated with cross-linking agents, e.g., glutaraldehyde, to improve the fiber's or thread's strength and/or various medically/surgically useful substances as described above. The collagen threads can be arranged to form various structures, such as a woven or non-woven fabric, bundle or braid, etc. by various techniques known in the art as described, e.g., in U.S. Pat. Nos. 5,171,273 and 5,378,469, each incorporated herein by reference.

For example, U.S. Pat. No. 5,171,273 describes the preparation of high-strength collagen fibers by dissolving Type I collagen in dilute hydrochloric acid, extruding the solution into a specific fiber formation buffer to reconstitute the collagen fibers. The reconstituted collagen fibers are subsequently cross-linked with glutaraldehyde or other chemical agents and treatments. The fibers are then processed into woven or non-woven materials.

U.S. Pat. No. 5,378,469 describes methods for the production of high strength collagen threads wherein collagen is extruded into a dehydrating agent, e.g., polyethylene glycol, which has a higher osmotic pressure than that of the collagen solution and a pH from about 5 to 10 which results in the formation of collagen threads. If desired, the collagen threads can be cross-linked using various chemical agents. The collagen threads are then utilized to form braided constructs, plied into yarn, and knitted.

Various constructs of the collagen fibers and threads can be formed utilizing well known techniques, e.g., braiding, plying, knitting, weaving, that are applied to processing natural fibers, e.g., cotton, silk, etc., and synthetic fibers made from synthetic bioabsorbable polymers, e.g., poly(glycolide) and poly(lactic acid), nylon, cellulose acetate, etc. See, e.g., Mohamed, American Scientist, 78: 530-541 (1990).

For example, aforementioned U.S. Pat. No. 5,378,469 describes the braiding of cross linked and non-cross linked collagen threads using a harness braiding machine (New England Butt Co., Providence, R.I.). Specifically, collagen thread is wound onto cylindrical stainless steel spools. The spools are then mounted onto the braiding carousel, and the collagen thread is then assembled in accordance with the instructions provided with the braiding machine. In one particular run, a braid was formed of four collagen threads, which consisted of two threads of uncrosslinked collagen and two threads of cross linked collagen.

The collagen threads may also be plied into yarns using the same methods and same machinery known to those skilled in the art in plying threads made out of other material, e.g., cotton, polyester, etc. For example, aforementioned U.S. Pat. No. 5,378,469 describes the production of a 60 ply yarn from non-cross linked collagen threads. Therein, 4 collagen threads were twisted together. Three of the resultant 4-ply strands were then twisted together in the opposite direction, and then 5 of the resultant 12 ply strands were twisted in the opposite direction.

The collagen threads and/or braided collagen threads or plied yarns can then be knitted into tubular or flat fabrics by using techniques known to those skilled in the art of producing fabrics manufactured from other types of threads. Various medically/surgically useful substances as described above can be incorporated in, or associated with, the braided, knitted, or woven collagen.

The biocompatible osteogenic band can also be fabricated in whole or in part from the submucosa of the intestine. Small intestine submucosa tissue is not osteogenic, but it can be made osteogenic by incorporating in, or associating with, the tendon tissue various osteogenic components as described above. Preparation of small intestine submucosa from a segment of small intestine is described, e.g., in U.S. Pat. No. 4,902,508, incorporated herein by reference. The segment of intestine which is obtained from an autogenic, allogeneic or xenogeneic source, is subjected to mild abrasion to remove the outer layers (the tunica serosa and the tunica muscularis) and the inner layers. The small intestine submucosa segment can be utilized in its entirety or alternatively, is cut into at least one elongated section or a plurality of elongated sections by methods well known to those skilled in the art. The small intestine submucosa is then rinsed with saline and stored in a hydrated or dehydrated state.

The biocompatible osteogenic band can also be fabricated in whole or in part from a synthetic biocompatible polymer or copolymer. As used herein, "bioabsorbable polymer" refers to a polymer or copolymer which is absorbed by the body. "Non-bioabsorbable polymer" refers to a polymer or copolymer which remain in the body without substantial bioerosion. As used herein, "biocompatible" with respect to bioabsorbable and non-bioabsorbable polymers means that the polymer does not elicit substantially adverse affects when implanted in living tissue. Examples of synthetic biocompatible bioabsorbable polymers or copolymers include, but are not limited to, poly(lactide), poly(glycolide), poly(epsilon-caprolactone), poly(p-dioxanone), poly(epsilon-caprolactone-co-p-dioxanone) and poly(lactide-co-glycolide) as described, e.g., in U.S. Pat. Nos. 5,705,181 and 5,393,594, each incorporated herein by reference; bioabsorbable block copolymers made of hard phase forming monomers, e.g., glycolide and lactide, and soft phase monomers, e.g., 1,4 dioxane-2-one and caprolactone, as described, e.g., in U.S. Pat. No. 5,522,841, incorporated herein by reference. Other bioabsorbable materials would include, e.g., natural materials such as cotton, and catgut. Examples of synthetic biocompatible non-bioabsorbable polymers include, but are not limited to, homopolymers and copolymers of polypropylene, polyamides, polyvinylchlorides, polysulfones, polyurethanes, polytetrafluoroethylene, etc. Biocompatible polymers are not osteogenic, but they can be made osteogenic by incorporating in, or associating with, the biocompatible polymers osteogenic components as described above. The biocompatible osteogenic band fabricated from the biocompatible polymer can have incorporated within, or be associated with, medically/surgically useful substances as described above.

In a particularly useful embodiment, the aforementioned osteogenic material making up the biocompatible osteogenic band can be wrapped with a monolithic piece, e.g., strips or sheets fabricated from a suitable material that is remodeled by the body and replaced over time with new bone tissue. For example, the osteogenic material can be wrapped or surrounded with demineralized bone strips cut from sheets which are composed of elongated bone particles, commercially known as GRAFTON® Flex (Osteotech, Eatontown, N.J.) as described, e.g., in aforementioned U.S. Pat. No. 5,507,813 and U.S. application Ser. No. 09/610,026, now issued under U.S. Pat. No. 6,863,694.

These demineralized bone strips can be affixed to the biocompatible osteogenic band by any convenient method, e.g., adhering the strips to the biocompatible osteogenic band utilizing adhesives, suturing the strips to the biocompatible osteogenic band, braiding the strips around the biocompatible osteogenic band, etc.

Figure 4:
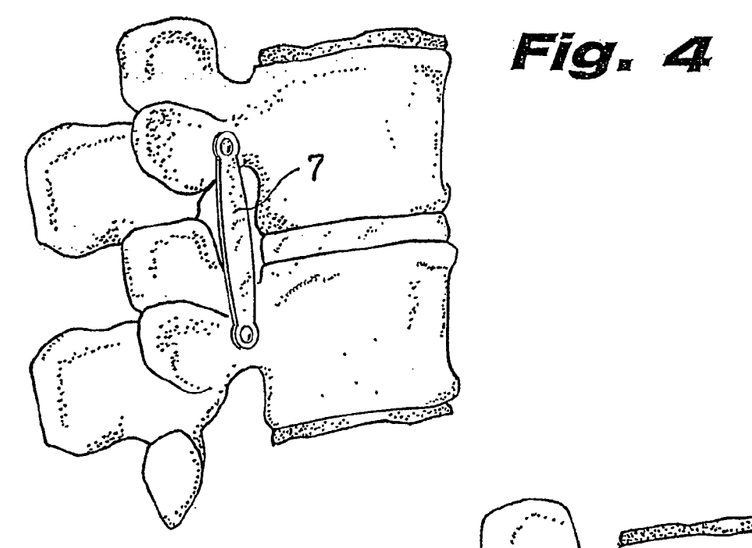
FIG. 4 is a diagrammatic left lateral view of the tension band described herein affixed to vertebrae of the lumbar region of the posterior spine.

The biocompatible osteogenic band described herein can be affixed to at least one site on each of two or more vertebrae at any region of the anterior or posterior spine in need of repair, preferably the posterior spine, and more preferably the lumbar region which bears heavier loads than other regions of the posterior spine. The site of affixation on each vertebra includes, but is not limited to, a vertebral body, pedicle, transverse process, mamillary process, inferior articular process, superior articular process, spinous process and accessory process. Preferably the site of affixation is the pedicle. FIG. 4 is a diagrammatic right lateral view of the described biocompatible osteogenic band 7 affixed to the transverse processes of lumbar vertebrae.

Selection of the particular two or more vertebrae for affixation of the biocompatible osteogenic band will depend on the particular region of the spine to be repaired and the nature of the spinal disorder. The two or more vertebrae can include adjacent vertebrae, alternating vertebrae, or a combination thereof. For example, the biocompatible osteogenic band can be affixed to adjacent lumbar vertebrae L4 and L5; alternating lumbar vertebrae L1, L3 and L5; and adjacent and alternating lumbar vertebrae L1, L2 and L4.

Figure 5:
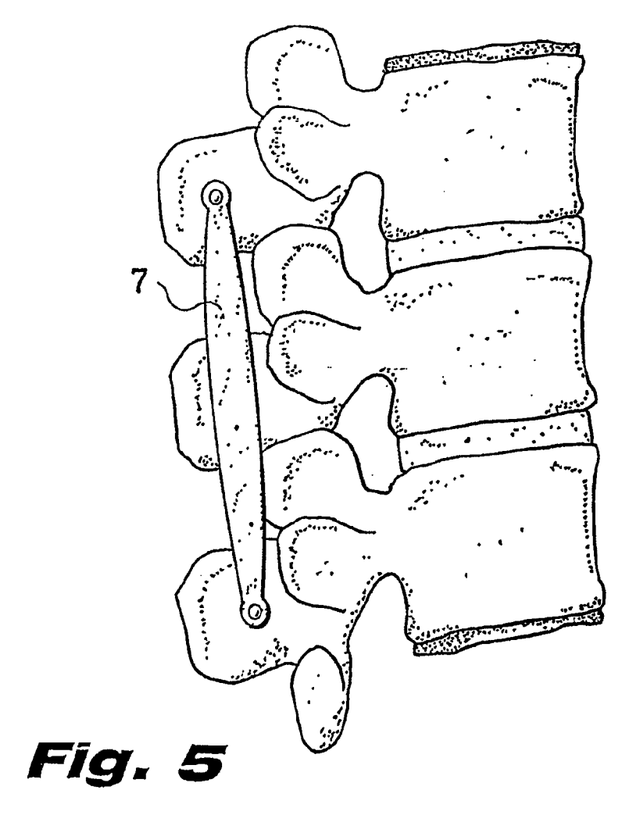
FIG. 5 is a diagrammatic posterior view of two tension bands symmetrically attached to each side of the lumbar region of the posterior spine.

Preferably, the biocompatible osteogenic band is affixed to two or more vertebrae on each side of the posterior spine in a symmetrical manner. For example, FIG. 5 shows a biocompatible osteogenic band 7 affixed to each side of the posterior spine on the third and fourth lumbar vertebrae. The biocompatible osteogenic band can be affixed to the vertebrae using any known surgical method, e.g., using bone screws, cement, hooks, friction, tying, pinning etc.

An example of a surgical procedure for affixing the described biocompatible osteogenic band to two vertebrae of the posterior spine comprises drilling a hole in the pedicle of each of the two vertebrae, wherein each hole is adapted to fit a pedicle screw. A pedicle screw having a threaded end portion is then screwed into the hole in each of the two pedicles using a screw driver. A biocompatible osteogenic band containing a hole fabricated at one of its ends is then affixed to the superior vertebra by inserting the threaded end portion of the pedicle screw fastened in the superior pedicle through the hole in the biocompatible osteogenic band. A nut is then secured to the threaded end portion of the fastened pedicle screw to secure the biocompatible osteogenic band to the superior vertebra. To load the linkage, i.e., to maintain the two or more vertebrae under tension, the posterior vertebrae between the two pedicle screws are then compressed. The degree to which the posterior vertebrae between the pedicle screws should be compressed will vary depending on the nature of the spinal disorder, the site of attachment of the ends of the biocompatible osteogenic band, the distance between the two vertebrae, and the amount of tension which needs to be placed on the posterior spine and can be determined by the surgeon during the surgical procedure. The other end of the biocompatible osteogenic band having a hole fabricated therein is then affixed to the posterior vertebra by inserting the threaded end portion of the pedicle screw fastened in the posterior vertebra through the hole at the other end of the tension band. A nut is then secured to the threaded end portion of the fastened pedicle screw in the posterior vertebra to secure the other end of the biocompatible osteogenic band to the posterior vertebra.

In a particularly useful embodiment, the present method is utilized in conjunction with other known methods for repairing the spine, particularly intervertebral spinal fusion, which is often performed to treat an anomaly involving an intervertebral disc caused by injury, disease or a degenerative disorder. Intervertebral spinal fusion is typically carried out by completely removing the intervertebral disc and inserting an anterior supporting structure 8, inside the interbody, interdiscal space to facilitate repair and healing (see FIG. 6). Over time, bone grows across the anterior supporting structure and the adjacent vertebrae grow together and fuse.

Various types of anterior supporting structures have been employed in intervertebral spinal fusion and are well known in the art such as a plug, bone dowel, prosthesis, cage device, bone graft, e.g., a machined allograft or autograft bone substitute, femoral ring, iliac crest graft, fibula, etc. For example, U.S. Pat. Nos. 4,834,757 and 4,878,915, each incorporated herein by reference, describe the use of plugs which are inserted into the disc space. In U.S. Pat. No. 4,834,757 the plug is a biocompatible composite cage which is intended to contain autologous or allogeneic bone to facilitate and promote bone ingrowth. In U.S. Pat. No. 4,878,915 the plug is a solid device containing barbs for biting into the bone as well as spaces between the barbs to facilitate bone ingrowth. U.S. Pat. No. 5,895,428, incorporated herein by reference, describes an implant having an upper member which pivots and is locked to a lower member. The upper portion of the upper member and the lower portion of the lower member engage adjacent vertebra and have ceramic surfaces which allow bone ingrowth. U.S. Pat. No. 5,899,939, incorporated herein by reference, describes a dowel-shaped bone-derived implant. U.S. Pat. No. 6,045,580, incorporated herein by reference, describes a bone implant derived from the iliac crest. U.S. Pat. No. 5,972,368, incorporated herein by reference, describes the use of bone graft substitute compositions and spacers which include a body composed of a deactivated bone graft. The body of the spacer can include flat spacers, bone dowels, cortical rings, bone chips and other suitably shaped bone pieces. Bone dowels from allogeneic femoral or tibial condyles are also commercially available from Osteotech, Inc. Medically/surgically useful substances and osteogenic components as described above with respect to the tension band can also be incorporated in, or associated with, the anterior supporting structure.

Figure 6:
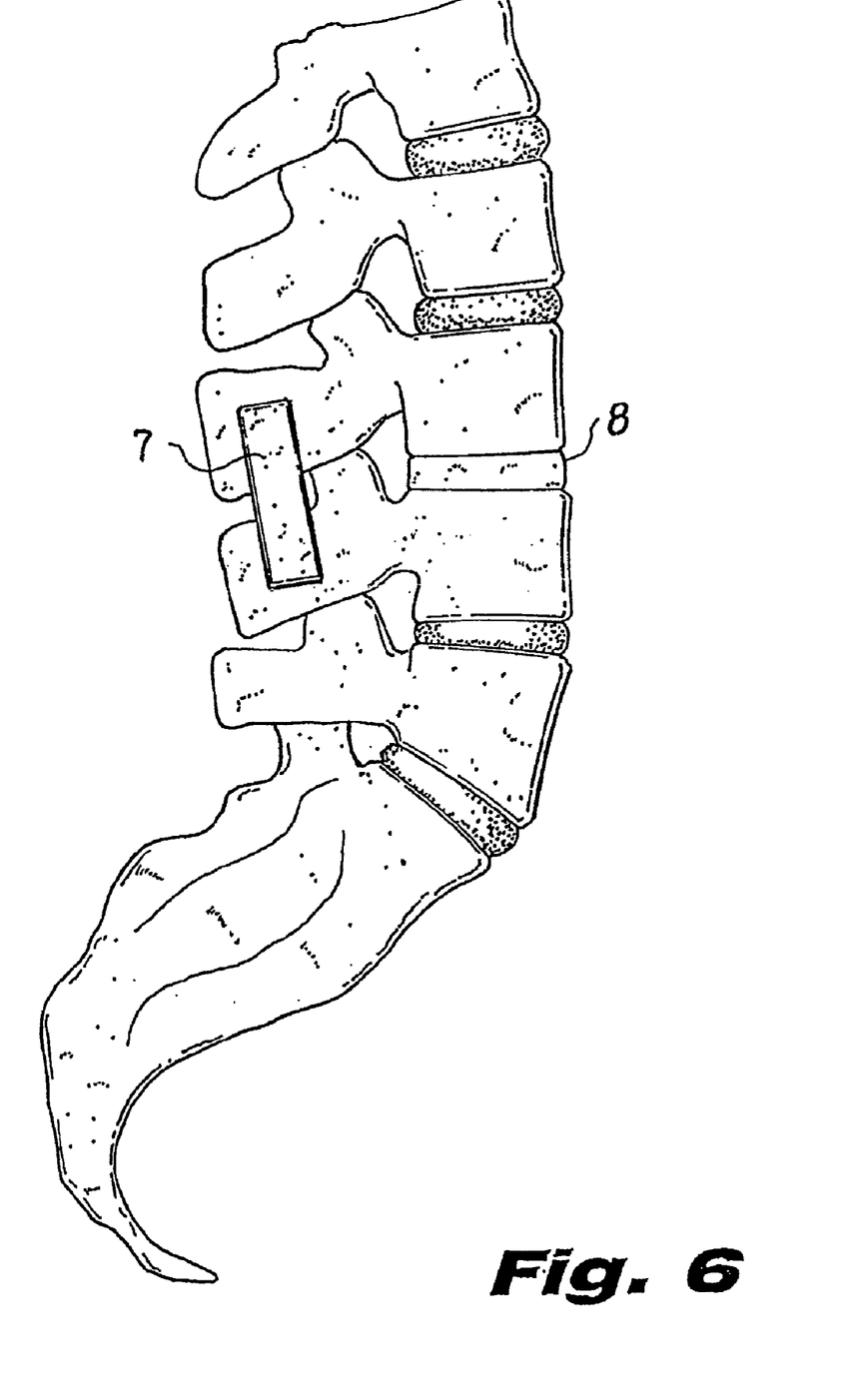
FIG. 6 is a diagrammatic lateral view of an osteogenic band affixed to vertebrae of the lumbar region of the posterior spine being used in conjunction with an anterior supporting structure.

FIG. 6 depicts a biocompatible osteogenic band 7 used in conjunction with an anterior supporting structure 8 to repair a spinal disorder. The anterior supporting structure 8 is inserted in the disc space between adjacent vertebrae prior to affixing the biocompatible osteogenic band 7 to the adjacent vertebrae of the posterior spine. For example, after the anterior supporting structure 8 is inserted in the disc space between the adjacent vertebrae, the biocompatible osteogenic band 7 can be affixed to the posterior spine by rocking the vertebra back using the anterior supporting structure 8 as a fulcrum and affixing the biocompatible osteogenic band 7 to the posterior spine.

In a particularly useful embodiment, a method of repairing a spinal disorder is provided which comprises inserting an anterior supporting structure in the disc space between adjacent vertebrae of a spine and then affixing a biocompatible osteogenic band fabricated of bone to two or more vertebrae of the spine, preferably the posterior side of the spine, to maintain the two or more vertebrae under tension. Preferably the biocompatible osteogenic band fabricated of bone comprises at least one elongated section of bone or a plurality of elongated sections of bone, and more preferably the bone section or sections are segmentally demineralized. In a most preferred embodiment, the segmentally demineralized bone sections are braided. In a particularly useful embodiment, the anterior supporting structure is a bone dowel.

While the present method of repairing a spinal disorder is useful in humans, it is also useful in treating many different types of animals, e.g., dogs, horses and the like.

The following example is meant to illustrate but not limit the invention.

EXAMPLE

Band Tensile Tests

Specimens were prepared from diaphyseal human cortical bone by first making transverse cuts to prepare a diaphyseal segment of the appropriate length, followed by longitudinal cuts. In this way, four segments were made having length 6 mm; and four segments were made having length 10 mm. The width and thickness of each test article was measured using a Mitutoyo Model 500-196CE digital caliper. Thicknesses were measured at three sites each and averaged (Table). Widths of the segments were also measured at three locations and averaged (Table). One specimen of the 6 mm length and one specimen of the 10 mm length were each covered on their ends by an elastic (synthetic rubber) balloon, fitted tightly around the piece. Other specimens were not masked in this way. All specimens were demineralized using 15 mL of 0.6N HCl acid per gram of weight, for 3 days, when all unmasked regions were well demineralized and flexible.

A uniaxial servo-hydraulic test machine (MTS model 858 Bionix) was used under displacement control to apply a constant tensile displacement to the test articles at a rate of 5 mm/min. The test article holding fixtures consisted of two vise-like grips, which were hand-tightened to attach each test specimen to the load cell (lower grip) and the actuator (upper grip). Tests terminated at failure of the test article. A 100 kN load cell was used to record load levels for all tests. As shown in the table below, average ultimate load and ultimate strength were 0.47 kN and 12.99 MPa respectively for the 6 cm long specimens, and 0.32 kN and 8.65 MPa respectively for the 10 cm long specimens.

TABLE

|  | Width 1 mm. | Width 2 mm. | Width 3 mm. | Thickness 1 mm. | Thickness 2 mm. | Thickness 3 mm. | Average Width mm. | Average Thickness mm. | Area mm.$^2$ | Ultimate Load kN | Ultimate Stress MPa |
|---|---|---|---|---|---|---|---|---|---|---|---|
| 6 cm.-1 (undemineralized ends) | 10.93 | 10.61 | 10.35 | 2.63 | 2.91 | 2.94 | 10.63 | 2.83 | 30.05 | 0.35 | 11.68 |
| 6 cm.-2 | 12.09 | 12.42 | 12.87 | 3.24 | 3.07 | 2.78 | 12.46 | 3.03 | 37.75 | 0.65 | 17.22 |
| 6 cm.-3 | 12.07 | 12.36 | 12.21 | 2.80 | 2.35 | 3.11 | 12.21 | 2.75 | 33.63 | 0.49 | 14.45 |
| 6 cm.-4 | 12.02 | 12.08 | 12.17 | 4.00 | 3.73 | 3.99 | 12.09 | 3.91 | 47.23 | 0.41 | 8.62 |
| 6 cm average | 11.78 | 11.86 | 11.9 | 3.17 | 3.02 | 3.21 | 11.85 | 3.13 | 37.17 | 0.47 | 12.99 |
| 10 cm.-1 (undemineralized ends) | 11.16 | 11.61 | 10.70 | 3.01 | 3.16 | 2.93 | 11.16 | 3.03 | 33.84 | 0.35 | 10.37 |
| 10 cm.-2 | 11.22 | 11.33 | 10.47 | 4.04 | 4.21 | 3.85 | 11.01 | 4.03 | 44.39 | 0.31 | 6.67 |
| 10 cm.-3 | 10.36 | 9.77 | 9.42 | 4.22 | 3.70 | 3.43 | 9.85 | 3.78 | 37.27 | 0.30 | 8.08 |
| 10 cm.-4 | 11.43 | 10.69 | 10.84 | 3.21 | 3.15 | 3.17 | 10.99 | 3.18 | 34.90 | 0.32 | 9.28 |
| 10 cm. average | 11.04 | 10.85 | 10.36 | 3.62 | 3.56 | 3.35 | 10.75 | 3.51 | 37.6 | 0.32 | 8.6 |

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A band for repair of spinal disorders, the band comprising: a flexible biocompatible osteogenic band comprising a plurality of elongated sections, the band having a first end and second end wherein the first end of the biocompatible osteogenic band is configured for affixation to one surface of a first vertebra and the second end of the biocompatible osteogenic band is configured for affixation to a corresponding surface of a second vertebra to maintain the joint formed by the adjacent vertebrae under tension; and
wherein the plurality of elongated sections have a configuration selected from the group consisting of braided, woven, a single twisted bundle, a helix, and combinations thereof.

2. The band of claim 1, wherein at least one of the elongated sections comprises bone.

3. The band of claim 2, wherein the at least one elongated section comprises cortical bone.

4. The band of claim 2, wherein the at least one elongated section comprises bone selected from the group consisting of autogenetic bone, allogeneic bone and xenogeneic bone.

5. The band of claim 2, wherein the at least one of the elongated section is demineralized.

6. The band of claim 5, wherein the at least one elongated section is chemically cross linked.

7. The band of claim 5, wherein the at least one of the elongated section is segmentally demineralized.

8. The band of claim 1, wherein at least one of the elongated sections comprises a synthetic biocompatible polymer or copolymer wherein the polymer or copolymer has been rendered ostegogenic.

9. The band of claim 8, wherein the biocompatible polymer is chosen from the group consisting of poly(lactic), polyglocolides, and poli(epsilon-caprolactone).

10. The band of claim 1, wherein at least one of the elongated sections comprises tendon tissue wherein the tendon tissue has been rendered osteogenic.

11. The band of claim 1, wherein at least one of the elongated sections comprises ligament tissue wherein the ligament tissue has been rendered osteogenic.

12. The band of claim 1, wherein at least one of the elongated sections comprises collagen tissue wherein the collagen tissue has been rendered osteogenic.

13. The band of claim 1, wherein at least one of the elongated sections comprises submucosa of the intestine wherein the submucosa has been rendered osteogenic.

14. The band of claim 1, wherein the biocompatible osteogenic band further comprises one or more substances selected from the group consisting of an antiviral agent, antimicrobial agent, antibiotic agent, biocidal/biostatic sugar, amino acid, peptide, vitamin, inorganic element, protein synthesis cofactor, hormone, endocrine tissue, synthesizer, enzyme, polymer-cell scaffold with parenchymal cells, angiogenic drug, collagen lattice, antigenic agent, cytoskeletal agent, cartilage fragment, chondrocytes, bone marrow cells, mesenchymal stem cells, natural extract, genetically engineered living cells, tissue transplant, demineralized bone powder, DNA, bioadhesive, bone morphogenic protein, osteoinductive factor, fibronectin, transforming growth factor-beta, endothelial cell growth factor, cementum attachment extracts, ketaserin, insulin-like growth factor, platelet derived growth factor, epidermal growth factor, interleukin, human alphathrombin, fibroblast growth factor, periodontal ligament chemotactic factor, growth hormone, bone digester, antitumor agent, immunosuppressant, permeation enhancer and nucleic acid.

15. The band of claim 1, wherein the biocompatible osteogenic band has a dimension between about 1 cm and about 1 meter in length, between 2 mm and about 30 mm in thickness, and between about 2 mm and about 30 mm in width.

16. The band of claim 1, wherein the helix comprises a plurality of elongated sections of bone bundled to form two or more bundles of multi-bone sections and wherein the multi-bone sections are wrapped to form a two or more bundle helix.

17. The band of claim 1, wherein at least one of the first and second ends is sealed with a polymer.

18. The band of claim 1, wherein at least one of the first end or the second end is threaded.

19. The band of claim 1, wherein at least one of the first end or the second end comprises an attachment hole.

20. The band of claim 1, wherein at least one of the first end or the second end comprises a loop formed by the plurality of elongated sections.

21. A biocompatible osteogenic band for repair or spinal disorders, the band comprising: a demineralized bone core;

and a weave of bioabsorable fibers surrounding the core; wherein the band comprises a first end and a second end and the first end of the biocompatible osteogenic band is configured for affixation to one surface of a first vertebra and the second end of the biocompatible osteogenic band is configured for affixation to a corresponding surface of a second vertebra to maintain the joint formed by the adjacent vertebrae under tension.

22. The band of claim 21, wherein the bioabsorable fibers comprises a synthetic biocompatible polymer wherein the synthetic biocompatible polymer is rendered osteogenic.

23. The band of claim 22, wherein the biocompatible polymer is chosen from the group consisting of poly(lactic), polyglocolides, and poli(epsilon-caprolactone).

24. The band of claim 21, wherein the weave of bioabsorbable fibers comprises demineralized bone strips.

25. The band of claim 21, wherein the core comprises a monolithic bone.

26. The band of claim 21, wherein the biocompatible osteogenic band further comprises one or more substances selected from the group consisting of an antiviral agent, antimicrobial agent, antibiotic agent, biocidal/biostatic sugar, amino acid, peptide, vitamin, inorganic element, protein synthesis cofactor, hormone, endocrine tissue, synthesizer, enzyme, polymer-cell scaffold with parenchymal cells, angiogenic drug, collagen lattice, antigenic agent, cytoskeletal agent, cartilage fragment, chondrocytes, bone marrow cells, mesenchymal stem cells, natural extract, genetically engineered living cells, tissue transplant, demineralized bone powder, DNA, bioadhesive, bone morphogenic protein, osteoinductive factor, fibronectin, transforming growth factor-beta, endothelial cell growth factor, cementum attachment extracts ketaserin, insulin-like growth factor, platelet derived growth factor, epidermal growth factor, interleukin, human alphathrombin, fibroblast growth factor, periodontal ligament chemotactic factor, growth hormone, bone digester, antifumor agent, immunosuppressant, permeation enhancer and nucleic acid.

27. The band of claim 21, wherein the demineralized bone core is segmentally demineralized.

* * * * *